United States Patent
Mourier et al.

(10) Patent No.: US 6,608,042 B2
(45) Date of Patent: Aug. 19, 2003

(54) PHARMACEUTICAL COMPOSITIONS CONTAINING OLIGOSACCHARIDES, THE NOVEL OLIGOSACCHARIDES AND PREPARATION THEREOF

(75) Inventors: Pierre Mourier, Charenton Le Pont (FR); Elisabeth Perrin, Evreux (FR); Christian Viskov, Ris Orangis (FR)

(73) Assignee: Aventis Pharma, S.A., Antony (FR)

( * ) Notice: Subject to any disclaimer, the term of this patent is extended or adjusted under 35 U.S.C. 154(b) by 0 days.

(21) Appl. No.: 09/817,428

(22) Filed: Mar. 26, 2001

(65) Prior Publication Data

US 2002/0019368 A1 Feb. 14, 2002

Related U.S. Application Data

(60) Provisional application No. 60/205,026, filed on May 18, 2000.

(30) Foreign Application Priority Data

Mar. 28, 2000 (FR) .............................................. 0003910

(51) Int. Cl.$^7$ ........................ A01N 43/04; A61K 31/715
(52) U.S. Cl. ............................. 514/54; 514/53; 514/56; 514/62; 536/18.7; 536/21; 536/54; 536/55; 536/55.1; 536/55.2; 536/123.1
(58) Field of Search ............................. 514/53, 54, 56, 514/62; 536/18.7, 21, 54, 55, 55.1, 55.2, 123.1

(56) References Cited

U.S. PATENT DOCUMENTS

| | | | | |
|---|---|---|---|---|
| 4,956,347 A | * | 9/1990 | Ban et al. | 514/54 |
| 5,145,841 A | * | 9/1992 | Cullis-Hill et al. | 514/54 |
| 5,389,618 A | | 2/1995 | Debrie | |
| 5,449,688 A | | 9/1995 | Wahl et al. | |
| 5,489,578 A | * | 2/1996 | Rosen et al. | 514/61 |
| 5,705,401 A | * | 1/1998 | Masters et al. | 436/518 |

FOREIGN PATENT DOCUMENTS

| | | | | |
|---|---|---|---|---|
| FR | 2548672 | 7/1983 | | |
| WO | 9001501 | 2/1990 | | |
| WO | WO 94/29352 | * 12/1994 | ........... | C08B/37/00 |
| WO | WO 95/09637 | * 4/1995 | ......... | A61K/31/715 |
| WO | 9614425 | 5/1996 | | |

OTHER PUBLICATIONS

Lee et al. Journal of Chromatography, 1981, vol. 212, pp. 65–73.*
McLean et al. Eur. J. Biochem. 1984, vol 145, pp. 607–615.*
Camu William et al; Purification of Embryonic Rat Motoneurons by Panning on a Monoclonal Antibody to the Low–Affinity NGF Receptor; J,. Neurosci.; vol. 44, pp. 59–70; (1992).

Chandler Charles E. et al; A Monoclonal Antibody Modulates the Interaction of Nerve Growth Factor with PC12 Cells; J. Biol. Chem.; vol. 259, No. 11; pp. 6882–2889; (1984).

Larnkjaer Anni et al; Isolation and Characterization of Hexasaccharides Derived from Heparin. Analysis by HPLC and Elucidation of Structure by 1 H NMR; Carbohydrate Research; vol. 266; pp. 37–52; (1995).

Rice Kevin G. et al; Study of Structurally Defined Oligosaccharide Substrates of Heparin and Heparan Monosulfate Lyases; Carbohydrate Research; vol. 190; pp. 219–233; (1989).

Saneto Russell P. et al; Neuronal and Glial Cells: Cell Culture of the Central Nervous System; Neurochemistry: A Practical Approach (eds. Turner, A. Bacheland, H.S.); pp. 27–63; (1987).

Schnaar Ronald L. et al; Separation of Cell Types from Embryonic Chicken and Rat Spinal Cord: Characterization of Motoneuron–Enriched Fractions; J. Neueosci.; vol. 1; No. 2; pp. 204–217; (1981).

Shellito Judd E. et al; Regulation of Nitric Oxide Release by Macrophages after Intratracheal Lipopolysaccharide; Am. J. Respir. Cell Mol. Biol.; vol. 13, pp. 45–53; (1993).

Yamashita Masamichi et al; Induction of Nitric Oxide Synthase by Lipopolysaccharide and its Inhibition by Auranolin in RAW 264.7 Cells; Eur. J. Pharmacol.; vol. 338, pp. 151–158; (1997).

* cited by examiner

Primary Examiner—James O. Wilson
Assistant Examiner—Patrick Lewis
(74) Attorney, Agent, or Firm—Irving Newman

(57) ABSTRACT

The present invention relates to pharmaceutical compositions containing as an active ingredient at least one oligosaccharide of formula:

(I)

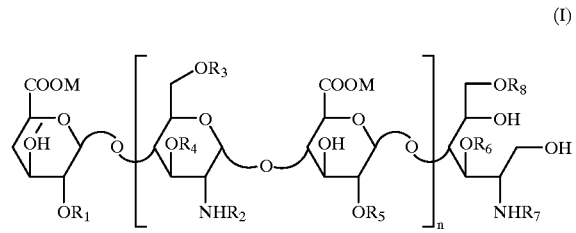

to novel oligosaccharides of formula (I), to mixtures thereof and to methods for their preparation.

34 Claims, No Drawings

PHARMACEUTICAL COMPOSITIONS CONTAINING OLIGOSACCHARIDES, THE NOVEL OLIGOSACCHARIDES AND PREPARATION THEREOF

CROSS REFERENCE TO RELATED APPLICATIONS

This application claims benefit of U.S. Provisional Application No. 60/205,206, filed on May 18, 2000 and of French Patent Application FR0003910 filed on Mar. 28, 2000.

The present invention relates to pharmaceutical compositions containing as active principle an oligosaccharide of formula:

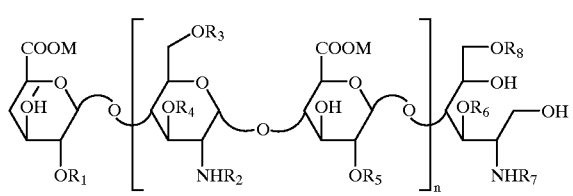

(I)

or to a mixture of these oligosaccharides, to the novel oligosaccharides of formula (I), to mixtures thereof and to methods for their preparation.

In formula (I), n is an integer from 0 to 25, $R_1$, $R_3$, $R_4$, $R_5$, $R_6$ and $R_8$, which may be identical or different, represent a hydrogen atom or an $SO_3M$ radical, $R_2$ and $R_7$, which may be identical or different, represent a hydrogen atom or an $SO_3M$ or $COCH_3$ radical, and M is sodium, calcium, magnesium or potassium.

These oligosaccharides thus comprise an even number of saccharides.

In formula (I), $R_4$ and $R_6$ are, preferably, hydrogen atoms.

Oligosaccharides of formula (I) for which n is equal to 0, and either $R_1$, $R_6$ and $R_8$ represent a hydrogen atom, $R_7$ represents an $SO_3M$ or $COCH_3$ radical and M is sodium, or $R_1$ and $R_6$ represent a hydrogen atom, $R_7$ represents a $COCH_3$ radical, $R_8$ represents an $SO_3M$ radical and M is sodium, or $R_6$ represents a hydrogen atom, $R_1$, $R_7$ and $R_8$ represent an $SO_3M$ radical and M is sodium have already been described by G. H. LEE et al., J. Chromat. 212, 65–73 (1981), but no pharmacological property is described for these products.

Oligosaccharides of formula (I) for which n is equal to 0, and either $R_6$ and $R_7$ represent hydrogen atoms, $R_1$ and $R_8$ represent an $SO_3M$ radical and M is sodium, or $R_1$, $R_6$ and $R_7$ represent a hydrogen atom, $R_8$ represents an $SO_3M$ radical and M is sodium, are described by M W McLEAN et al., Eur. J. Biochem., 1984, 145, 607, without any indication of pharmacological activity.

The pharmaceutical compositions which are preferred are those containing an oligosaccharide of formula (I) for which:

n is an integer from 0 to 10, and in particular from 0 to 6, and even more particularly from 1 to 6.

$R_1$, $R_2$, $R_3$, $R_5$, $R_7$ and $R_8$ are identical or different, and represent a hydrogen atom or an $SO_3M$ radical, and in particular $R_1$, $R_2$, $R_3$, $R_5$, $R_7$ and $R_8$ are $SO_3M$ radicals, M is sodium.

The pharmaceutical compositions which are particularly preferred are those containing an oligosaccharide of formula (I) for which:

n is equal to 0, $R_1$, $R_7$ and $R_8$ represent an $SO_3M$ radical, $R_6$ represents a hydrogen atom and M is sodium, n is equal to 1, $R_1$, $R_2$, $R_3$, $R_5$, $R_7$ and $R_8$ represent an $SO_3M$ radical, $R_4$ and $R_6$ represent a hydrogen atom and M is sodium, n is equal to 2, $R_1$, $R_2$, $R_3$, $R_5$, $R_7$ and $R_8$ represent an $SO_3M$ radical, $R_4$ and $R_6$ represent a hydrogen atom and M is sodium, n is equal to 3, $R_1$, $R_2$, $R_3$, $R_5$, $R_7$ and $R_8$ represent an $SO_3M$ radical, $R_4$ and $R_6$ represent a hydrogen atom and M is sodium, n is equal to 4, $R_1$, $R_2$, $R_3$, $R_5$, $R_7$ and $R_8$ represent an $SO_3M$ radical, $R_4$ and $R_6$ represent a hydrogen atom and M is sodium.

The oligosaccharides of formula (I), with the exception of those for which n is equal to 0 and either $R_1$, $R_6$ and $R_8$ represent a hydrogen atom, $R_7$ represents an $SO_3M$ or $COCH_3$ radical and M is sodium, or $R_1$, and $R_6$ represent a hydrogen atom, $R_7$ represents a $COCH_3$ radical, $R_8$ represents an $SO_3M$ radical and M is sodium, or $R_6$ represents a hydrogen, $R_1$, $R_7$ and $R_8$ represent an $SO_3M$ radical and M is sodium, or $R_6$ and $R_7$ represent hydrogen atoms, $R_1$ and $R_8$ represent an $SO_3M$ radical and M is sodium, or $R_1$, $R_6$ and $R_7$ represent a hydrogen atom, $R_8$ represents an $SO_3M$ radical and M is sodium, are novel and, as such, form part of the invention.

The oligosaccharides of formula (I) can be prepared by reaction of an alkali metal borohydride or a quaternary ammonium borohydride with oligosaccharides of formula:

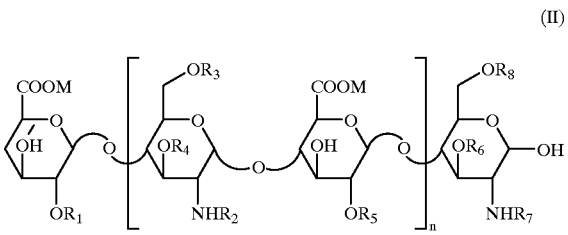

(II)

in which n is an integer from 0 to 25, $R_1$, $R_3$, $R_4$, $R_5$, $R_6$ and $R_8$, which may be identical or different, represent a hydrogen atom or an $SO_3M$ radical, $R_2$ and $R_7$, which may be identical or different, represent a hydrogen atom or an $SO_3M$ or $COCH_3$ radical, and M is sodium, calcium, magnesium or potassium.

This reaction is carried out in aqueous medium, at a temperature in the vicinity of 25° C., at a pH between 7 and 10, and preferably between 9 and 10, for the entire duration of the reaction. The pH is maintained by addition of a sodium hydroxide solution at 0.5 mol/l. The reaction is stopped by acidification of the reaction medium, for example by addition of acetic acid until a pH between 4 and 5 is obtained.

As alkali metal borohydrides, mention may be made of lithium borohydride, sodium borohydride and potassium borohydride.

As a quaternary ammonium borohydride, mention may be made of tetrabutylammonium borohydride.

The oligosaccharides of formula (II) can be obtained by gel chromatography separation of a mixture of oligosaccharides (III) obtained by enzymatic depolymerization of heparin or basic depolymerization of the benzyl ester of heparin or of a benzyl ester of semi-synthetic heparin.

This chromatography is carried out on columns filled with gel of polyacrylamide-agarose type, such as that sold under the trade mark Ultrogel ACA202$^R$ (Biosepra). Preferably, an array of polyacrylamide agarose gel columns is used. The number of columns used is adapted as a function of the volume, the gel and the oligosaccharides to be separated. The mixture is eluted with a solution containing a phosphate buffer and sodium chloride. Preferably, the phosphate buffer solution is a solution containing 0.02 mol/l of $NaH_2PO_4$/$Na_2HPO_4$ (pH 7) containing 0.1 mol/l of sodium chloride. Detection of the various fractions is carried out by UV spectrometry (254 nm) and ionic spectrometry (IBF). The fractions thus obtained can then be optionally purified, for example by SAX (strong anion exchange) chromatography according to the methods known to those skilled in the art and in particular according to the methods described by K. G. Rice and R. J. Linhardt, Carbohydrate Research 190, 219–233 (1989), A. Larnkjaer, S. H. Hansen and P. B. Ostergaard, Carbohydrate Research, 266, 37–52 (1995) and in patent WO 90/01501 (Example 2). The fractions are then lyophilized, and then desalified on a gel-filled column such as a column of Sephadex G10® gel (Pharmacia Biochemicals).

When the purification is not carried out by SAX chromatography, the lyophilizates can be optionally purified by simple or fractional precipitation according to the methods known to persons skilled in the art and in particular according to the method described in patent FR 2 548 672. Generally, the process is performed according to the following procedure:

The lyophilized fraction to be purified is dissolved, at 25° C., in about ten volumes of distilled water. On adding methanol or ethanol, the desired oligosaccharide is precipitated, while monitoring its enrichment by HPLC chromatography (high performance liquid chromatography). The addition of methanol or ethanol is determined as a function of the desired yield and purity of said oligosaccharide. Similarly, this operation can be carried out in several successive steps starting with the initial solution of lyophilizate. For this, more of the insolubilizing agent (methanol or ethanol) is added portionwise and the precipitate obtained after each addition is isolated. The precipitates thus prepared are analyzed by HPLC chromatography. Depending on the desired yield and purity, the suitable fractions of precipitate are combined.

According to a variant of the present invention, the lyophilized fraction to be purified can be dissolved in 10 to 200 volumes of water containing from 0 to 30% sodium acetate. The percentage of sodium acetate will be preadjusted as a function of the nature of the oligosaccharide to be treated (a function of the size). On adding methanol, the desired oligosaccharide is precipitated while monitoring its enrichment by HPLC chromatography (high performance liquid chromatography). The addition of methanol is determined as a function of the desired yield and purity of said oligosaccharide. Similarly, this operation can be carried out in several successive steps starting with the initial solution of lyophilizate. For this, more of the insolubilizing agent (methanol) is added portionwise and the precipitate obtained after each addition is isolated. The precipitates thus prepared are analyzed by HPLC chromatography. Depending on the desired yield and purity, the suitable fractions of precipitate are combined.

For the intermediates of formula (II) for which n=0, 1 or 2, it is preferable to start with a mixture (III) obtained by enzymatic depolymerization.

This depolymerization is carried out by means of heparinase I (EC 4.2.2.7), in a pH 7 phosphate buffer solution, in the presence of sodium chloride and of BSA (bovine serum albumin), at a temperature between 10 and 18° C., and preferably 15° C., for 8 to 10 days, and preferably 9 days. The depolymerization is stopped, for example, by heating the reaction medium at 100° C. for 2 minutes, and the mixture is recovered by lyophilization. It is preferable to use 7 IU of heparinase I per 25 g of heparin. The phosphate buffer solution generally comprises 0.05 mol/l of $NaH_2PO_4$/$Na_2HPO_4$ (pH 7) in the presence of 0.1 mol/l of sodium chloride. The BSA concentration is generally 2%.

For the intermediates of formula (II) for which n=0, 1, 2, 3 or 4, it is preferable to start with a mixture (III) obtained by depolymerizing a benzyl ester of heparin.

The benzyl ester of heparin can be prepared according to the methods described in patents U.S. Pat. No. 5,389,618, EP 40 144 and FR 2 548 672. The degree of esterification will preferably be between 50 and 100%. Preferably, it will be between 70 and 90%.

The depolymerization is carried out in aqueous medium, by means of an alkali metal hydroxide (for example lithium hydroxide, sodium hydroxide, potassium hydroxide or cesium hydroxide) or of a quaternary ammonium hydroxide (for example tetrabutylammonium hydroxide), preferably at a molarity between 0.1 and 0.2 mol/l, at a temperature between 40 and 80° C., for 5 to 120 minutes. In one preferred mode, the process is performed for 5 to 15 minutes, at a temperature between 60 and 70° C., with a 0.15 mol/l sodium hydroxide solution. The depolymerization reaction is stopped by neutralization by addition of an acid such as acetic acid. After addition of 10% by weight per volume of sodium acetate, the oligosaccharide mixture is precipitated by adding methanol, preferably 2 volumes per 1 volume of reaction medium, and filtered.

According to one preferred aspect of the invention, the oligosaccharide mixture obtained after chemical depolymerization, in the form of an aqueous solution, is enriched by ultrafiltration through membranes with a suitable nominal cut-off threshold (of the Pellicon type made of regenerated cellulose, sold by Millipore); the type of membrane being adapted as a function of the type of enriched oligosaccharides to be recovered. For the oligosaccharides (II) for which n=0, a membrane with a nominal cut-off threshold of 1 kDa will be used, for the oligosaccharides (II) for which n=1, a 1 kDa or 3 kDa membrane will be used, for the oligosaccharides (II) for which n=2, a 3 kDa membrane will be used, for the oligosaccharides (II) for which n=3 or 4, a 5 kDa membrane will be used. During this operation, the permeate is recovered and the retentate is discarded. Thus, the fraction of enriched product can represent from 50 to 10% of the initial oligosaccharide mixture, while at the same time conserving at least 80% of the desired oligosaccharide.

For the intermediates of formula (II) for which n=0 to 25, it is preferable to start with a mixture (III) obtained by depolymerizing a benzyl ester of semi-synthetic polysaccharide sulfate. The benzyl ester of semi-synthetic polysaccharide sulfate is prepared from semi-synthetic polysaccharide sulfates obtained from polysaccharide K5, and according to the methods described in patents WO 94/29352 and WO 96/14425. The esterification, depolymerization and recovery conditions are the same as those described above for the benzyl ester of heparin.

In all the preceding processes, the initial heparin can be of porcine, ovine, caprine or bovine origin and can be obtained from the mucus, lungs or hides of the animals. Preferably, a heparin from porcine or ovine mucus or from bovine lung is used, and even more preferably from porcine mucus or from bovine lung.

The oligosaccharides of formula (I) have anti-inflammatory properties and can thus be used for preventing or treating diseases associated with an inflammatory process involving the production of cytotoxic substances such as nitrogen monoxide (NO), whose inducible form is released in particular by neutrophils or macrophages when these neutrophils or macrophages migrate and are activated in a tissue. The migration, activation and adhesion of neutrophils takes place in tissue regions which have been made ischemic following an occlusion or a spasm of an artery which vascularizes this tissue. These ischemias can arise either in the brain (cerebrovascular accident) or in the myocardium (myocardial infarction) or in the lower limbs (known as peripheral ischemias). The oligosaccharides of formula (I) can thus be used for preventing and/or treating neurodegenerative diseases for which cerebral inflammation plays a deleterious role which can lead to death, among which mention may be made of cerebral ischemias, cardiac ischemias (myocardial infarction), peripheral ischemias, traumas of the central nervous system and in particular cranial, spinal and craniospinal traumas, multiple sclerosis, neuropathic pain and peripheral neuropathies, motoneuron diseases including amyotrophic lateral sclerosis, progressive spinal atrophy, infantile muscular atrophy and primary lateral sclerosis, neuro-AIDS, Alzheimer's disease, Parkinson's disease and Huntington's chorea and certain forms of osteoarthritis, in particular with articular localization.

The anti-inflammatory activity of these products is demonstrated in vivo in the test of production of NOx (nitrite and nitrate) induced by a lipopolysaccharide (LPS) originating from $E.\ coli$, according to the protocol described by M. YAMASHITA et al., Eur. J. Pharmacol, 338, 2, 151–158 (1997) or J. E. SHELLITO et al., Am. J. Respir. Cell Mol. Biol., 13, 1, 45–53 (1995).

0.5 mg/kg of the oligosaccharide is injected into male CD1 mice (Charles River, 25–35 g) at T0 via intravenous bolus, and 1 or 2 mg/kg of the oligosaccharide are injected subcutaneously at T+15 minutes. At T+30 minutes, 100 mg/kg of lipopolysaccharide (LPS) originating from $E.\ coli$ (Sigma L3129, serotype 0127:B8) are administered. At T+3 hours 1 or 2 mg/kg of the oligosaccharide are again injected subcutaneously. At T+5 hours 30 minutes, a blood sample is collected by ocular puncture, and the concentrations of NOx (nitrite and nitrate) in the plasma are determined by the Griess calorimetric method, after reduction of the nitrate to nitrite with nitrate reductase in the following way: 12 ml of the plasma sample are mixed with 88 ml of deionized water and incubated in the dark for 1 hour at room temperature with 40 ml of phosphate buffer (0.31M, pH 7.5), 20 ml of β-NADPH (reduced nicotinamide adenine dinucleotide phosphate) (0.86 mM), 20 ml of FDA (flavin adenine dinucleotide) (0.11 mM) and 20 ml of nitrate reductase (2 U/ml) (Boehringer Mannheim). 10 ml of $ZnSO_4$ (1M) are added to precipitate the proteins, and, after mixing, the samples are centrifuged at 20,000×g for 5 minutes. Finally, 50 ml of the supernatant are incubated for 10 minutes at room temperature with 100 ml of the Griess reagent (1% sulfanilamide in a phosphoric acid/0.1% naphthylethylenediamine mixture in deionized water (V/V)). The optical densities are read at 540 nm with a microplate spectrophotometer, each point being determined twice. $KNO_3$ and $NaNO_2$ are used as standards for the colorimetric method.

In this test, the oligosaccharides according to the invention inhibit the formation of NOx by more than 50%.

Moreover, the oligosaccharides of formula (I) increase the survival and growth of motoneurons and are therefore particularly useful in preventing and/or treating motoneuron diseases such as amyotrophic lateral sclerosis, progressive spinal atrophy, infantile muscular atrophy and primary lateral sclerosis.

It is known that motoneuron cultures die by apoptosis if they are prepared in the absence of a trophic support (BDNF, NT5, for example). It has now been found that the oligonucleotides according to the invention enable motoneurons to survive and grow. This activity was assayed on cocultures of astrocytes and of motoneurons deprived of neurotrophic factors, according to the following protocol:

Cultures Enriched in Motoneurons:

The cultures enriched in motoneurons are prepared using the centrifugation method described by R. L. Schnaar and A. E. Schaffner, J. Neurosci., 1, 204–217 (1981) and modified by W. Camu and C. E. Henderson, J. Neurosci. Methods, 44, 59–70 (1992). Spinal cords of rat E15 embryos are sterilely dissected and the dorsal spinal notochords are removed. They are then cut up and incubated for 15 minutes at 37° C. in PBS (phosphate buffer saline: 137 mM NaCl, 2.68 mM Kcl, 6.45 mM $Na_2HPO_4$, 1.47 mM $KH_2PO_4$) to which 0.05% of trypsin has been added. The dissociation of the cells is completed by trituration with the end of a 1 ml pipette in the culture medium supplemented with 0.1% of bovine serum albumin (BSA) and with 0.1 mg/ml of DNAase. The cell suspension layered out onto a band of 6.5% weight/volume metrizamide in L15 medium (sold by Gibco BRL) and centrifuged at 500 g for 15 minutes. The band at the interface containing the motoneurons is recovered, diluted in L15 medium and incubated for 45 minutes at room temperature in culture dishes pre-coated with anti-mouse IgG and with MC192 hybridoma supernatant (Chandler C E et al., J. Biol. Chem., 259, 6882 (1984)). The suspended cells are washed with L15 medium and the motoneurons are eluted, with gentle stirring, with the MC192 hybridoma supernatant. The motoneurons are plated out at a density of 650 cells per 24 mm in culture dishes, on astrocyte monolayers, in L15 medium to which sodium bicarbonate (22 mM), coalbumin (0.1 mg/ml), putrescine (0.1 mM), insulin (5 µg/ml), sodium selenite (31 nM), glucose (20 mM), progesterone (21 nM), penicillin (100 IU/ml) and streptomycin (100 µg/ml) have been added. The cultures are maintained at 37° C. in a humidified atmosphere at 5% of $CO_2$.

Culturing of Spinal Cord Astrocytes:

The astrocytes are obtained from rat embryos according to the method of R. P. Saneto and J. De Vellis, in Neurochemistry, a practical approach (A. J. Turner and H. S. St John) IRL Press, Oxford-Washington DC, pp. 27–63 (1987), slightly modified. The spinal cords are sterilely dissected and the meninges and dorsal ganglia are removed. Five to ten spinal cords are transferred into PBS (phosphate buffer saline: 137 mM NaCl, 2.68 mM Kcl, 6.45 mM $Na_2HPO_4$, 1.47 mM $KH_2PO_4$) and cut up before being incubated at 37° C. for 25 minutes in PBS to which 0.25% of trypsin has been added. The enzymatic treatment is stopped by adding 10 ml of Dubelco-Eagle modified medium (DMEM) to which 10% of foetal calf serum (FCS) has been added, and the cells are collected by centrifugation. Another mechanical dissociation step is carried out using the end of a 1 ml pipette. The cells are plated out at a density of $1.5 \times 10^6$ cells per 25 $cm^2$ of culture medium in DMEM containing 10% of FCS. After 2 days in vitro, the cultures are fed every day throughout the duration of the study. When a visible monolayer of cells is obtained, the cells are shaken for 48 hours at 250 rpm and, the following day, the monolayers are treated with cytosine arabinoside ($10^{-5}$ M) for 48 hours. The astrocyte monolayers are then amplified to a density of five per 35 mm on culture plates, for 25 $cm^2$ culture flasks at the start of the study.

The spinal astrocyte cultures are composed of more than 98% cells which are immunoreactive for glial fibrilary acidic protein (GFAP).

The astrocyte monolayers are exposed either to PBS alone (controls) or to the product to be tested in solution in PBS for 24 hours at the concentration of 0.1 ng/ml to 10 ng/ml. The astrocyte monolayers are then washed with DMEM and maintained for 2 hours with culture medium to which the motoneurons are added. Two hours after feeding, and for 2 to 3 days, the vehicle or the product to be tested is again added to the culture medium.

Immunochemical Identification of the Motoneurons:

The cells are fixed in 4% of paraformaldehyde and 0.1% of glutaraldehyde in PBS (pH 7.4 at 4° C. for 15 minutes). The cultures are then washed and the nonspecific sites are blocked with 2% of bovine serum albumin (BSA) in PBS and 0.1% of Triton X100®. These cultures are successively incubated with $p75^{LNGRF}$ antibodies (article by Chandler, cited above), overnight at 4° C., and with biotinylated goat serum (1/125, Gibco) and streptavidin-peroxidase (1/200, Gibco) for 60 minutes. The antibodies are visualized using the DAB/hydrogen peroxide reaction.

Cell Counting and Statistical Analysis

The cells which are immunoreactive for the low activity neutrophin receptor $p75^{lngfr}$ and which exhibit neurites longer than the diameters of 4 cells are considered to be viable motoneurons. The number of motoneurons is evaluated by counting the labelled cells in a surface area of 0.825 $cm^2$ under a microscope with a 200 fold magnification. The values are expressed as the number of motoneurons per $cm^2$ or a percentage of the number of motoneurons present in the cultures maintained in the absence of trophic factor compared to the control. The experiments are carried out at least 3 times.

The statistical analyses are carried out using the Student's test (t-test).

Using pretreatments with the oligosaccharides of the present invention, the number of motoneurons which grow on the astrocyte monolayer is increased from 20 to 50%.

The following examples are representative of the preparation of the oligosaccharides of formula (I) and of the intermediates.

In these examples, the abbreviations have the following meanings:

ΔIs: (4-deoxy-2-O-sulfo-α-L-threo-hex-enopyranosyluronic acid)-(1→4)-2-deoxy-2-sulfoamino-6-O-sulfo-α-D-glucopyranose, tetrasodium salt, or ΔUAp2S-(1→4)-α-D-GlcNp2S6S Is: (2-sulfo-α-L-idopyranosyluronic acid)-(1→4)-2-deoxy-2-sulfoamino-6-O-sulfo-α-D-glucopyranose, tetrasodium salt, (2-sulfo-α-L-idopyranosyluronic acid)-(1→4)-2-deoxy-6-O-sulfo-2-sulfoamino-α-D-glucopyranose, tetrasodium salt, or α-L-idoAp2S-(1→4)-α-D-GlcNp2S6S IIs: (α-L-idopyranosyluronic acid)-(1→4)-2-deoxy-6-O-sulfo-2-sulfoamino-α-D-glucopyranose, trisodium salt, or α-L-idoAp-(1→4)-α-D-GlcNp2S6S IIIs: (2-sulfo-α-L-idopyranosyluronic acid)-(1→4)-2-deoxy-2-sulfoamino-α-D-glucopyranose, trisodium salt, or α-L-idoAp2S-(1→4)-α-D-GlcNp2S IdoAp: idopyranosyluronic acid GlcNp: 2-amino-2-deoxyglucopyranose ΔUap: 4-deoxy-α-L-threo-hexenopyranosyluronic acid S: sulfate.

EXAMPLES OF PREPARATION OF THE INTERMEDIATE MIXTURES OF FORMULA (II)

Example A

Preparation of the Oligosaccharides of Formula (II) for which n=0, 1 and 2 by Enzymatic Depolymerization and Separation 25 g of heparin are dissolved in 250 ml of a phosphate buffer solution containing 0.05 mol/l of $NaH_2PO_4/Na_2HPO_4$ (pH=7), 0.02 mol/l of sodium chloride and 2% BSA (bovine serum albumin). 7 IU of heparinase I (EC 4.2.2.2.7) are introduced into the mixture, and the solution obtained is cooled to 15° C. and then kept at this temperature throughout the depolymerization reaction. The progress of the reaction is monitored by taking aliquot samples at intervals, which are analyzed by gel permeation chromatography. After 9 days, the enzymatic reaction is stopped by heating the reaction medium at 100° C. for two minutes. The cooled mixture is then lyophilized. An oligosaccharide mixture (III) is thus obtained.

The oligosaccharide mixture (III) obtained is then chromatographed according to the following method: the chromatography is carried out on columns filled with polyacrylamide-agarose gel known under the name Ultrogel ACA 202, and the mixture is eluted with a solution containing a phosphate buffer (0.02 mol/l $NaH_2PO_4/Na_2HPO_4$) pH=7 and 0.1 mol/l of sodium chloride. The detection is performed by UV spectrometry (254 nm) and ionic spectrometry (IBF). The products can optionally be purified by SAX (strong anion exchange) chromatography or by fractional precipitation according to the method described in patent FR 2 548 672. The product fractions recovered are lyophilized and then desalified on a column filled with Sephadex G10® gel (Pharmacia Biochemicals).

By this method, 3 g of disaccharide ΔIs and 1100 mg of a hexasaccharide mixture typically containing 55% of ΔIs-Is-Is derivative, 35% of ΔIs-Is-IIs and 10% of ΔIs-Is-IIIs are obtained. The latter mixture can be purified according to the methods known to persons skilled in the art in order to separate each one of the constituents therefrom, or can be used in its current state for conversion into reduced derivatives of formula (I).

Example B

Preparation of the Oligosaccharides of Formula (II) for which n=0, 1, 2, 3 or 4 by Depolymerization of the Benzyl Ester of Heparin and Separation a—Preparation of the benzyl ester of heparin The benzyl ester of heparin is prepared according to Example 3 of U.S. Pat. No. 5,389,618.

b—Depolymerization 100 g of benzyl ester of heparin are dissolved in 1.9 l of demineralized water. The mixture is brought to 60° C. with stirring. After obtaining a homogeneous solution, about 35 ml of a 23% sodium hydroxide solution are introduced in a single portion. After reaction for 10 minutes, the solution is then cooled and neutralized with 80 ml of an approximately 2 N acetic acid solution. 10% by weight/volume of sodium acetate is added to this solution. The oligosaccharide mixture is precipitated by adding about 2 volumes of methanol. The precipitate is isolated by filtration, washed twice with methanol and dried under reduced pressure at 50° C. After drying, 73.8 g of an oligosaccharide mixture (II) are obtained.

c—Enrichment in oligosaccharide for which n=1

30 g of the oligosaccharide mixture obtained above are dissolved in about 35 volumes of water. This solution is ultrafiltered through a 3 kDa membrane (Pellicon). When 600 ml of permeate have been drawn, the retentate is diluted with 500 ml of water. The operation is continued until an additional 450 ml of permeate have been drawn. The two fractions of permeate are combined and then concentrated to dryness under reduced pressure. 6.1 g of a yellowish-white solid are obtained. Analysis of the solid by gel permeation chromatography indicates that it contains about 30% of oligosaccharide of formula (II) for which n=1.

d—Fractionation of the ultrafiltered oligosaccharide mixtures

The enriched mixture is fractionated on columns filled with polyacrylamide-agarose gel known under the name Ultrogel ACA 202 (4 columns in series, of diameter 10 cm and length 50 cm, are used). 5 g of the mixture enriched by ultrafiltration are dissolved in 25 ml of water, and then eluted with a 0.2 mol/l sodium chloride solution at a rate of 5 ml/min. 25-ml fractions are collected at the bottom of the column. Detection of the products is performed by UV spectrometry (254 nm) and ionic spectrometry (IBF). The fractions of product for which n=1 are recovered, lyophilized and then desalified on a column filled with Sephadex G10 gel. After lyophilization, 1 g of tetrasaccharide typically containing 70% of ΔIs-Is derivative of formula II ($R_1$, $R_2$, $R_3$, $R_5$, $R_7$, $R_8$=$SO_3Na$; $R_4$, $R_6$=H and M=Na) is obtained. The ΔIs-Is derivative can optionally be purified by SAX (strong anion exchange) chromatography or, according to a preferred aspect, by fractional precipitation according to the method described in patent FR 2 548 672 and the variant described in the present invention.

Examples of Preparation of the Oligosaccharides of Formula (I)

Example 1

A solution, at 25° C., of 300 mg of an oligosaccharide of formula (II) in which n is equal to 0, $R_1$, $R_7$ and $R_8$ represent an $SO_3M$ radical, $R_6$ represents a hydrogen atom and M is sodium, in 2 ml of water, is introduced into a reactor. 212 mg of sodium borohydride are added in a single portion, with stirring. The pH is then adjusted to between 9 and 10 by addition of a 0.5 mol/l sodium hydroxide solution. After 12 hours, acetic acid is added gradually until a pH between 4 and 5 is obtained. The mixture is stirred for 1 hour, and then the pH is readjusted to 6.7 by addition of 0.5 mol/l sodium hydroxide. The mixture is then concentrated to dryness at 50° C. under reduced pressure. The concentrate is dispersed, with magnetic stirring, in 10 ml of methanol. After sedimentation overnight, the suspension is filtered through a Whatman GF/B membrane. The solid on the filter is dissolved by passing 2 portions of 10 ml of distilled water. This solution is then concentrated to dryness at 50° C. under reduced pressure. 580 mg of a white solid are obtained. The solid is then dispersed, with magnetic stirring, in 15 ml of methanol. After stirring for 30 minutes, the suspension is filtered through a Whatman GF/B membrane. The cake is dissolved by passing 2 portions of 10 ml of distilled water. The solution obtained is concentrated to dryness at 50° C. under reduced pressure. 250 mg of an oligosaccharide of formula (I) for which n is equal to 0, $R_1$, $R_7$ and $R_8$ represent an $SO_3M$ radical, $R_6$ represents a hydrogen atom and M is sodium are thus obtained, in the form of a mixture of diastereoisomers. The sugars constituting the disaccharides are noted from I to II, I being the reduced residue and II being the unsaturated uronic acid residue [(4-deoxy-2-O-sulfo-α-L-threohex-4-enopyranosyluronic acid-(1→4)-2-deoxy-6-O-sulfo-2-sulfoamino-D-glucitol, tetrasodium salt); (4-deoxy-2-O-sulfo-α-L-threo-hex-4-enopyranosyluronic acid-(1→4)-2-deoxy-6-O-sulfo-2-sulfoamino-D-mannitol, tetrasodium salt): proton spectrum in $D_2O$, 600 MHz, T=305 K, δ in ppm: 3.38 (1H, m, H-2$^{(I)}$), 3.70 and 3.75 (1H each, respectively dd, J=6 and 12 Hz and dd, J=5 and 12 Hz, 2H-1$^{(I)}$), 3.86 (1H, t, J=5 Hz, H-3$^{(I)}$), 4.13 (1H, dd, J=8 and 11 Hz, H-6$^{(I)}$), 4.18 (1H, m, H-4$^{(I)}$), 4.25 (2H, m, H-6$^{(I)}$ and H-3$^{(II)}$, 4.35 (1H, m, H-5$^{(I)}$), 4.65 (1H, m, H-2$^{(II)}$), 5.67 (1H, s, H-1$^{(II)}$), 6.00 (1H, d, J=5 Hz, H-4$^{(II)}$)].

Example 2

A solution, at 25° C., of 60 mg of an oligosaccharide of formula (II) in which n is equal to 0, $R_1$, $R_2$, $R_3$, $R_5$, $R_7$ and $R_8$ represent an $SO_3M$ radical, $R_4$ and $R_6$ represent a hydrogen atom and M is sodium, in 1.2 ml of water, is introduced into a reactor. 18 mg of sodium borohydride are added in a single portion, with stirring. The pH is then adjusted to between 9 and 10 by addition of a 0.5 mol/l sodium hydroxide solution. After 12 hours, acetic acid is added gradually until a pH between 4 and 5 is obtained. The mixture is stirred for 1 hour, and then 5 ml of methanol are added. The suspension is filtered through a Whatman GF/B membrane, and the recovered solid is rinsed with twice 0.5 ml of methanol. After drying, 42 mg of an oligosaccharide of formula (I) for which n is equal to 1, $R_1$, $R_2$, $R_3$, $R_5$, $R_7$ and $R_8$ represent an $SO_3M$ radical, $R_4$ and $R_6$ represent a hydrogen atom and M is sodium are obtained, in the form of a mixture of diastereoisomers. The sugars constituting the tetrasaccharides are noted from I to IV, I being the reduced residue and IV being the unsaturated uronic acid residue [(4-deoxy-2-O-sulfo-α-L-threo-hex-4-enopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-2-sulfoamino-6-O-sulfo-D-glucitol, octasodium salt); (4-deoxy-2-O-sulfo-α-L-threo-hex-4-enopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-D-mannitol, octasodium salt): proton spectrum in $D_2O$, 400 MHz, T=298 K, δ in ppm: 3.25 (1H, dd, J=10 and 3 Hz, H-2$^{(III)}$), 3.37 (1H, m, H-2$^{(I)}$), 3.59 (1H, m, H-3$^{(III)}$), 3.75 (2H, m, 2H-1$^{(I)}$), 3.79 (1H, t, J=9 Hz, H-4$^{(III)}$), 3.86 (1H, m, H-3$^{(I)}$), between 4.05 and 4.40 (10H, broad peak, H-4$^{(I)}$/H-5$^{(I)}$/2H-6$^{(I)}$, H-2$^{(II)}$/H-3$^{(II)}$/H-4$^{(II)}$), 2H-6$^{(III)}$, H-3$^{(IV)}$), 4.58 (1H, m, H-2$^{(IV)}$), 4.60 (1H, m, H-5$^{(II)}$), 5.27 (1H, d, J=4 Hz, H-1$^{(III)}$), 5.42 (1H, d, J=4 Hz, H-1$^{(II)}$), 5.47 (1H, d, J=2 Hz, H-1$^{(IV)}$), 5.95 (1H, d, J=5 Hz, H-4$^{(IV)}$)].

Example 3

A solution, at 25° C., of 100 mg of an oligosaccharide of formula (II) in which n is equal to 2, $R_1$, $R_2$, $R_3$, $R_5$, $R_7$ and $R_8$ represent an $SO_3M$ radical, $R_4$ and $R_6$ represent a hydrogen atom and M is sodium, in 2 ml of water, is introduced into a reactor. 20 mg of sodium borohydride are added in a single portion, with stirring. The pH is then adjusted to between 9 and 10 by addition of a 0.5 mol/l sodium hydroxide solution. After 12 hours, acetic acid is added gradually until a pH between 4 and 5 is obtained. The mixture is stirred for 1 hour, and then the pH is readjusted to 6.7 by addition of 0.5 mol/l sodium hydroxide. The mixture is then diluted with a sufficient quantity of distilled water to obtain 20 ml. 2.5 g of sodium acetate are added and 3 volumes of methanol are run in. The suspension is filtered on a Whatman GF/B membrane, and the recovered solid is rinsed with twice 2 ml of methanol. After drying, 61 mg of an oligosaccharide of formula (I) for which n is equal to 2, $R_1$, $R_2$, $R_3$, $R_5$, $R_7$ and $R_8$ represent an $SO_3M$ radical, $R_4$ and $R_6$ represent a hydrogen atom and M is sodium are obtained, in the form of a mixture of diastereoisomers. The sugars constituting the hexasaccharides are noted from I to VI, I being the reduced residue and VI being the unsaturated uronic acid residue. [(4-Deoxy-2-O-sulfo-α-L-threo-hex-4-enopyranosyluronic acid-(1→4)-2-deoxy-2-sulfoamino-6-O-sulfo-α-D-glucopyranosyl-(1→4)-2-O-sulfo-α-L-idopyranosyluronic acid-(1→4)-2-deoxy-2-sulfoamino-6-O-sulfo-α-D-glucopyranosyl-(1→4)-2-O-sulfo-α-L- idopyranosyluronic acid-(1→4)-2-deoxy-2-sulfoamino-6-O-sulfo-D-glucitol, dodecasodium salt); (4-deoxy-2-O-sulfo-α-L-threo-hex-4-enopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-D-mannitol, dodecasodium salt): proton spectrum in $D_2O$, 600 MHz, T=305 K, δ in ppm: 3.25 (2H, m, $H-2^{(III)\ and\ (V)}$), 3.38 (1H, m, $H-2^{(I)}$), 3.61 (2H, t, J=10 Hz, $H-3^{(III)\ and\ (V)}$), between 3.70 and 3.83 (4H, broad peak, $2H-1^{(I)}$ and $H-4^{(III)\ and\ (V)}$), 3.86 (1H, t, J=5 Hz, $H-3^{(I)}$), 4.00 (2H, m, $H-5^{(III\ and\ V)}$), 4.07 (1H, m, $H-4^{(IV)}$), 4.08 (1H, m, $H-4^{(I)}$), between 4.10 and 4.45 (13H, broad peak, H-5 $^{(I)}/2H-6^{(I)}$, $H-2^{(II)}/H-3^{(II)}/H-4^{(II)}$, $2H-6^{(III)}$, $H-2^{(IV)}/H-3^{(IV)}$, $2H-6^{(V)}$, $H-3^{(VI)}$), 4.60 (1H, s, $H-2^{(VI)}$), 4.62 (1H, s, $H-5^{(VI)}$), 4.78 (1H, s, $H-5^{(IV)}$), 5.17 (1H, s, $H-1^{(IV)}$), 5.28 (1H, d, J=4 Hz, $H-1^{(II)}$), 5.38 (1H, d, J=3 Hz, $H-1^{(V)}$), 5.44 (1H, d, J=3 Hz, $H-1^{(III)}$), 5.47 (1H, d, J=2 Hz, $H-1^{(VI)}$), 5.96 (1H, d, J=5 Hz, $H-4^{(VI)}$)].

Example 4

A solution, at 25° C., of 100 mg of an oligosaccharide of formula (II) in which n is equal to 3, $R_1$, $R_2$, $R_3$, $R_5$, $R_7$ and $R_8$ represent an $SO_3M$ radical, $R_4$ and $R_6$ represent a hydrogen atom and M is sodium, in 2 ml of water, is introduced into a reactor. 30 mg of sodium borohydride are added in two portions, with stirring. The pH is then adjusted to between 9 and 10 by addition of a 0.5 mol/l sodium hydroxide solution. After 12 hours, acetic acid is added gradually until a pH between 4 and 5 is obtained. The mixture is stirred for 1 hour, and then the pH is readjusted to 6.7 by addition of 0.5 mol/l sodium hydroxide. The mixture is then diluted with a sufficient quantity of distilled water to obtain 20 ml. 2 g of sodium acetate are added and 3 volumes of methanol are run in. The suspension is filtered on a Whatman GF/B membrane, and the recovered solid is rinsed with twice 1 ml of methanol. After drying, 68 mg of a white solid are obtained. After HPLC (high pressure liquid chromatography) monitoring, since the product is not totally reduced, all the preceding operations are entirely repeated. After drying, 45 mg of an oligosaccharide of formula (I) for which n is equal to 3, $R_1$, $R_2$, $R_3$, $R_5$, $R_7$ and $R_8$ represent an $SO_3M$ radical, $R_4$ and $R_6$ represent a hydrogen atom and M is sodium are obtained, in the form of a mixture of diastereoisomers. The sugars constituting the octasaccharides are noted from I to VIII, I being the reduced residue and VIII being the unsaturated uronic acid residue, [(4-deoxy-2-O-sulfo-α-L-threo-hex-4-enopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-2-sulfoamino-6-O-sulfo-α-D-glucopyranosyl-(1→4)-2-O-sulfo-α-L-idopyranosyluronic acid-(1→4)-2-deoxy6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-D-glucitol, hexadecasodium salt); (4-deoxy-2-O-sulfo-α-L-threo-hex-4-enopyranosyluronic acid-(1→4)-2-deoxy-6-O-sulfo-2-sulfoamino-α-D-glucopyranosyl-(1→4)-2-O-sulfo-α-L-idopyranosyluronic acid-(144)-2-deoxy-6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-D-mannitol, hexadecasodium salt): proton spectrum in $D_2O$, 600 MHz, T=305 K, δ in ppm: 3.25 (3H, m, $H-2^{(III)}$, $H-2^{(v)}$, $H2^{(VII)}$), 3.38 (1H, m, $H-2^{(I)}$, 3.61 (3H, m, $H-3^{(III)}$, $H-3^{(V)}$, $H-3^{(VII)}$), between 3.70 and 3.83 (5H, broad peak, $2H-1^{(I)}$ and $H-4^{(III)}$, $H-4^{(V)}$, $H4^{(VII)}$), 3.86 (1H, t, J=5 Hz, $H-3^{(I)}$), 4.00 (3H, m, $H-5^{(III)}$, $H-5^{(V)}$, $H-5^{(VII)}$), 4.08 (3H, m, $H-4^{(I)}$, $H4^{(IV)}$, $H-4^{(VI)}$), between 4.10 and 4.45 (17H, broad peak, $H-5^{(I)}/2H-6^{(I)}$, $H-2^{(II)}/H-3^{(II)}/H-4^{(II)}$, $2H-6^{(III)}$, $H-2^{(IV)}/H3^{(IV)}$, $2H-6^{(V)}$, $H-2^{(VI)}/H-3^{(VI)}$, $2H-6^{(VII)}$, $H-3^{(VIII)}$), 4.59 (1H, s, $H-2^{(VIII)}$), 4.62 (1H, s, $H-5^{(II)}$), 4.78 (2H, s, $H-5^{(IV)}$, $H-5^{(VI)}$), 5.17 (2H, s, $H-1^{(IV)}$, $H-1^{(VI)}$), 5.28 (1H, d, J=4 Hz, $H-1^{(II)}$), 5.38 (2H, m, $H-1^{(V)}$, $H-1^{(VII)}$), 5.44 (1H, d, J=3 Hz, $H-1^{(III)}$), 5.47 (1H, s, $H-1^{(VIII)}$), 5.96 (1H, d, J=s Hz, $H-4^{(VIII)}$) ].

Example 5

A solution, at 25° C., of 65 mg of an oligosaccharide of formula (II) in which n is equal to 4, $R_1$, $R_2$, $R_3$, $R_5$, $R_7$ and $R_8$ represent an $SO_3M$ radical, $R_4$ and $R_6$ represent a hydrogen atom and M is sodium, in 1.2 ml of water, is introduced into a reactor. 18 mg of sodium borohydride are added in a single portion, with stirring. The pH is then adjusted to between 9 and 10 by addition of a 0.5 mol/l sodium hydroxide solution. After 12 hours, acetic acid is added gradually until a pH between 4 and 5 is obtained. The mixture is stirred for 1 hour, and then the pH is readjusted to 6.7 by addition of 0.5 mol/l sodium hydroxide. The mixture is then diluted with 3 ml of an aqueous solution of 10% sodium acetate, and 3 volumes of methanol (12 ml) are run in. The suspension is filtered, and the recovered solid is rinsed with 3 ml of methanol. After drying, 54 mg of an oligosaccharide of formula (I) for which n is equal to 4, $R_1$, $R_2$, $R_3$, $R_5$, $R_7$ and $R_8$ represent an $SO_3M$ radical, $R_4$ and $R_6$ represent a hydrogen atom and M is sodium are obtained, in the form of a mixture of diastereoisomers. The sugars constituting the decasaccharides are noted from I to X, I being the reduced residue and X being the unsaturated uronic acid residue. [(4-Deoxy-2-O-sulfo-α-L-threo-hex-4-enopyranosyluronic acid-(1→4)-2-deoxy-2-sulfoamino-6-O-sulfo-α-D-glucopyranosyl-(1→4)-2-O-sulfo-α-L-idopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-D-glucitol, eicosodium salt); (4-deoxy-2-O-sulfo-α-L-threo-hex-4-enopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-α-D-glucopyranosyl-(14)-2-O-sulfo-α-L-idopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-α-D-glucopyranosyl-(1→4)-2-O-sulfo-α-L-idopyranosyluronic acid-(1→4)-2-deoxy-6-O-sulfo-2-sulfoamino-D-mannitol, eicosodium salt): proton spectrum in $D_2O$, 600 MHz, T=303 K, δ in ppm: 3.23 (4H, m, $H-2^{(III)}$, $H-2^{(V)}$, $H-2^{(VII)}$, $H-2^{(IX)}$), 3.35 (1H, m, $H-2^{(I)}$), 3.59 (4H, m, $H-3^{(III)}$, $H-3^{(V)}$, $H-3^{(VII)}$, $H-3^{(IX)}$) between 3.65 and 3.80 (6H, m), 3.85 (1H, m, $H-3^{(I)}$), between 3.90 and 4.40 (29H, m), 4.57 (1H, m, $H-2^{(X)}$), 4.59 (1H, m, $H-5^{(II)}$), 4.75 (3H, m, $H-5^{(IV)}$, $H-5^{(VI)}$, $H-5^{(VIII)}$), 5.15 (3H, m, $H-1^{(IV)}$, $H-1^{(VI)}$, $H-1^{(VIII)}$), 5.25 (1H, m, $H-1^{(II)}$), 5.37 (3H, m, $H-1^{(V)}$, $H-1^{(VII)}$, $H-1^{(IX)}$, $H-1^{(VIII)}$), 5.42 (1H, m, $H-1^{(III)}$), 5.45 (1H, m, $H-1^{(X)}$), 5.93 (1H, d, J=5 Hz, $H-4^{(X)}$).

The medicinal products according to the invention comprise, as active principle, at least one oligosaccharide of formula (I) or a mixture of oligosaccharides of formula (I), in the form of a composition in which it is combined with any other pharmaceutically compatible product, which can be inert or physiologically active. The medicinal products according to the invention can be used via the intravenous, subcutaneous, oral, rectal, topical or pulmonary (inhalation) route.

The sterile compositions for intravenous or subcutaneous administration are generally aqueous solutions. These compositions can also contain adjuvants, in particular wetting agents, isotonifying agents, emulsifiers, dispersants and stabilizers. The sterilization can be carried out in several ways, for example by aseptic filtration, by incorporating sterilizing agents into the composition or by irradiation. They can also be prepared in the form of sterile solid compositions which can be dissolved, at the time of use, in sterile water or any other injectable sterile medium.

Solid compositions for oral administration which can be used are tablets, pills, powders (gelatin capsules or cachets) or granules. In these compositions, the active principle is mixed with one or more inert diluents, such as starch, cellulose, sucrose, lactose or silica, under a stream of argon.

These compositions can also comprise substances other than diluents, for example one or more lubricants such as magnesium stearate or talc, an agent for promoting oral absorption, a dye, a coating (dragees) or a varnish.

Liquid compositions for oral administration which can be used are pharmaceutically acceptable solutions, suspensions, emulsions, syrups and elixirs containing inert diluents such as water, ethanol, glycerol, plant oils or liquid paraffin. These compositions can comprise substances other than diluents, for example wetting products, sweeteners, thickeners, flavorings or stabilizers.

The compositions for rectal administration are suppositories or rectal capsules which contain, besides the active product, excipients such as cocoa butter, semi-synthetic glycerides or polyethylene glycols.

The compositions for topical administration can be, for example, creams, lotions, eye drops, throat sprays, nasal drops or aerosols.

The doses depend upon the desired effect, the duration of the treatment and the route of administration used; they are generally between 0.5 mg and 10 mg per kg per day, subcutaneously, i.e. 3 to 60 mg per day for a 60 kg adult.

In general, the doctor will determine the appropriate dosage as a function of the age, the weight and all the other personal factors of the individual to be treated.

The invention also relates to the use of the oligosaccharides according to the invention for preparing a medicinal product which is useful for preventing or treating diseases linked to an inflammatory process involving the production of nitrite oxide (NO), or which is useful for the survival and growth of motoneurons.

The invention is particularly advantageous for the use of the oligosaccharides of formula (I) for preparing medicinal products which are useful for preventing and treating cerebral ischaemias, cardiac ischaemias or peripheral vascular ischaemias, osteoarthritis, traumas of the central nervous system, cranial, spinal and craniospinal traumas, multiple sclerosis, neuropathic pain and peripheral neuropathies, motoneuron disease, amyotrophic lateral sclerosis, neuro-AIDS, Alzheimer's disease, Parkinson's disease and Huntington's chorea.

The invention also relates to the method for preventing and/or for treating diseases associated with an inflammatory process involving the production of cytotoxic substances such as nitrite oxide (NO) and of diseases linked to the survival and growth of motoneurons. The oligosaccharides of formula (I) can thus be used for preventing and/or treating neurodegenerative diseases for which cerebral inflammation plays a deleterious role which can lead to death, among which mention may be made of cerebral ischemias, cardiac ischemias (myocardial infarction), peripheral ischemias, traumas of the central nervous system and in particular cranial, spinal and craniospinal traumas, multiple sclerosis, neuropathic pain and peripheral neuropathies, motoneuron diseases including amyotrophic lateral sclerosis, progressive spinal atrophy, infantile muscular atrophy and primary lateral sclerosis, neuro-AIDS, Alzheimer's disease, Parkinson's disease and Huntington's chorea and certain forms of osteoarthritis, in particular with articular localization.

The present invention also relates to the method for preventing and/or treating motoneuron diseases such as amyotrophic lateral sclerosis, progressive spinal atrophy, infantile muscular atrophy and primary lateral sclerosis.

What is claimed is:

1. A pharmaceutical composition comprising one or more oligosaccharides of formula:

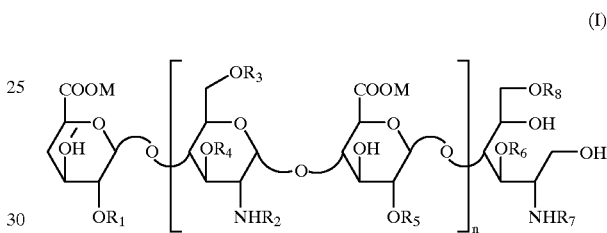

(I)

in which n is an integer from 0 to 25, each of $R_1$, $R_3$, $R_4$, $R_5$, $R_6$ and $R_8$, which may be identical or different, is hydrogen or an $SO_3M$ radical, each of $R_2$ and $R_7$, which may be identical or different, is hydrogen or an $SO_3M$ or $COCH_3$ radical, and M is sodium, calcium, magnesium or potassium, excluding, however, those oligosaccharides wherein (1), n is equal to 0 and (2) either (a) each of $R_1$, $R_6$ and $R_8$ is hydrogen, $R_7$ is an $SO_3M$ or $COCH_3$ radical and M is sodium, or (b) each of $R_1$ and $R_6$ is hydrogen $R_7$ is a $COCH_3$ radical, $R_8$ is a $SO_3M$ radical and M is sodium, or (c) $R_6$ is hydrogen, each of $R_1$, $R_7$ and $R_8$ is an $SO_3M$ radical and M is sodium, or (d) each of $R_6$ and $R_7$ is hydrogen, each of $R_1$ and $R_8$ is an $SO_3M$ radical and M is sodium, or (e) each of $R_1$ and $R_6$ and $R_7$ is hydrogen, $R_8$ is an $SO_3M$ radical and M is sodium.

2. A pharmaceutical composition according to claim 1, wherein $R_4$ and $R_6$ both are hydrogen.

3. A pharmaceutical composition according to claim 1, wherein n is an integer from 0 to 10.

4. A pharmaceutical composition according to claim 2, wherein n is an integer from 0 to 10.

5. A pharmaceutical composition according to claim 3, wherein n is an integer from 0 to 6.

6. A pharmaceutical composition according to claim 4, wherein n is an integer from 0 to 6.

7. A pharmaceutical composition according to claim 5, wherein n is an integer from 1 to 6.

8. A pharmaceutical composition according to claim 6, wherein n is an integer from 1 to 6.

9. A pharmaceutical composition according to claim 1, wherein n is equal to 1, each of $R_1$, $R_2$, $R_3$, $R_5$, $R_7$ and $R_8$ is an $SO_3M$ radical, each of $R_4$ and $R_6$ is hydrogen and M is sodium.

10. A pharmaceutical composition according to claim 1, wherein n is equal to 2, each of $R_1$, $R_2$, $R_3$, $R_5$, $R_7$ and $R_8$ is an $SO_3M$ radical, each of $R_4$ and $R_6$ is hydrogen and M is sodium.

11. A pharmaceutical composition according to claim 1, wherein n is equal to 3, each of $R_1$, $R_2$, $R_3$, $R_5$, $R_7$ and $R_8$ is an $SO_3M$ radical, each of $R_4$ and $R_6$ is hydrogen and M is sodium.

12. A pharmaceutical composition according to claim 1, wherein n is equal to 4, each of $R_1$, $R_2$, $R_3$, $R_5$, $R_7$ and $R_8$ is an $SO_3M$ radical, each of $R_4$ and $R_6$ is hydrogen and M is sodium.

13. An oligosaccharide of formula:

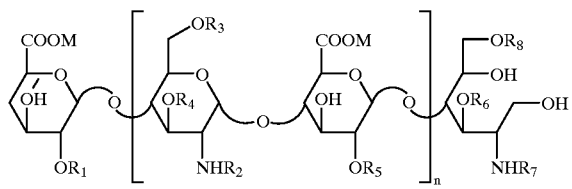

(I)

in which n is an integer from 0 to 25, each of $R_1$, $R_3$, $R_4$, $R_5$, $R_6$ and $R_8$, which may be identical or different, is hydrogen or an $SO_3M$ radical, each of $R_2$ and $R_7$, which may be identical or different, is hydrogen or an $SO_3M$ or $COCH_3$ radical, and M is sodium, calcium, magnesium or potassium, excluding, however, those oligosaccharides wherein (1), n is equal to 0 and (2) either (a) each of $R_1$, $R_6$ and $R_8$ is hydrogen, $R_7$ is an $SO_3M$ or $COCH_3$ radical and M is sodium, or (b) each of $R_1$ and $R_6$ is hydrogen $R_7$ is a $COCH_3$ radical, $R_8$ is an $SO_3M$ radical and M is sodium, or (c) $R_6$ is hydrogen, each of $R_1$, $R_7$ and $R_8$ is an $SO_3M$ radical and M is sodium, or (d) each of $R_6$ and $R_7$ is hydrogen, each of $R_1$ and $R_8$ is an $SO_3M$ radical and M is sodium, or (e) each of $R_1$, $R_6$ and $R_7$ is hydrogen, $R_8$ is an $SO_3M$ radical and M is sodium.

14. An oligosaccharide according to claim 13, wherein each of $R_4$ and $R_6$ is hydrogen.

15. An oligosaccharide according to claim 13, wherein n is an integer from 0 to 10.

16. An oligosaccharide according to claim 14, wherein n is an integer from 0 to 10.

17. An oligosaccharide according to claim 15 wherein n is an integer from 0 to 6.

18. An oligosaccharide according to claim 16 wherein n is an integer from 0 to 6.

19. An oligosaccharide according to claim 17, wherein n is an integer from 1 to 6.

20. An oligosaccharide according to claim 18, wherein n is an integer from 1 to 6.

21. An oligosaccharide according to claim 13, wherein n is 0, each of $R_1$, $R_7$ and $R_8$ is an $SO_3M$ radical, $R_6$ is hydrogen and M is sodium.

22. An oligosaccharide according to claim 13, wherein n is 1, each of $R_1$, $R_2$, $R_3$, $R_5$, $R_7$ and $R_8$ is an $SO_3M$ radical, each of $R_4$ and $R_6$ is hydrogen and M is sodium.

23. An oligosaccharide according to claim 13, wherein n is 2, each of $R_1$, $R_2$, $R_3$, $R_5$, $R_7$ and $R_8$ is an $SO_3M$ radical, each of $R_4$ and $R_6$ is hydrogen and M is sodium.

24. An oligosaccharide according to claim 13, wherein n is 3, each of $R_1$, $R_2$, $R_3$, $R_5$, $R_7$ and $R_8$ is an $SO_3M$ radical, each of $R_4$ and $R_6$ is hydrogen and M is sodium.

25. A method for preparing an oligosaccharide of claim 13, this method comprising reacting an alkali metal borohydride or a quaternary ammonium borohydride with an oligosacchande of formula:

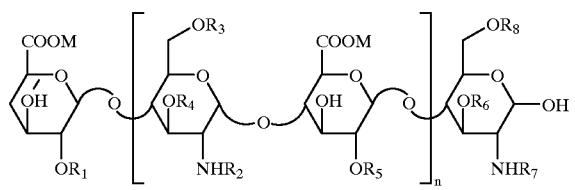

(II)

wherein n is an integer from 0 to 25, each of $R_1$, $R_2$, $R_3$, $R_4$, $R_5$, $R_6$, $R_7$ and $R_8$ is as defined in claim 13, and isolating the resulting oligosaccharide.

26. The method according to claim 25, wherein the reaction is carried out in aqueous medium, at a temperature of about 25° C. and at a pH of from 7 to 10.

27. The method according to claim 25, wherein the reaction pH is from 9 to 10.

28. The method according to claim 26, wherein the reaction pH is from 9 to 10.

29. The method according to claim 25, wherein the alkali metal borohydride or quaternary ammonium borohydride is lithium borohydride, sodium borohydride, potassium borohydride or tetrabutylammonium borohydride.

30. The method according to claim 26, wherein the alkali metal borohydride or quaternary ammonium borohydride is lithium borohydride, sodium borohydride, potassium borohydride or tetrabutylammonium borohydride.

31. The method according to claim 27, wherein the alkali metal borohydride or quaternary ammonium borohydride is lithium borohydride, sodium borohydride, potassium borohydride or tetrabutylammonium borohydride.

32. A method of treating diseases associated with an inflammatory process involving the production of nitrite oxide (NO), this method comprising administering to a patient in need thereof, an effective amount to prevent or treat such disease of at least on oligosaccharide of formula:

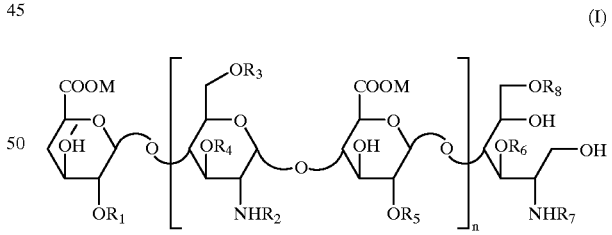

(I)

wherein n is an integer from 0 6 o 25, each of $R_1$, $R_3$, $R_4$, $R_5$, $R_6$, and $R_8$, which may be identical or different, is hydrogen or an $SO_3M$ radical, each of $R_2$, and $R_7$, which may be identical or different, is hydrogen or an $SO_3M$ or $COCH_3$ radical, and M is sodium, calcium, magnesium or potassium.

33. A method of treating diseases associated with an inflammatory process involving the production of nitrite oxide (NO), this method comprising administering to a patient in need thereof, an effective amount to prevent or treat such disease of at least one oligosaccharide of formula:

of formula:

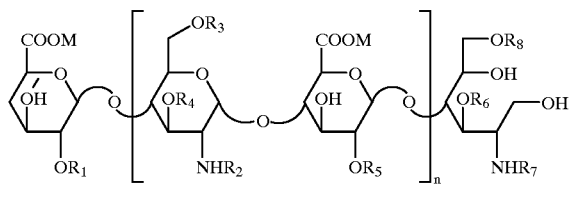

(I)

wherein n is an integer from 0 to 25, each of $R_1$, $R_3$, $R_4$, $R_5$, $R_6$, and $R_8$, which may be identical or different, is hydrogen or an $SO_3M$ radical, each of $R_2$ and $R_7$, which may be identical or different, is hydrogen or an $SO_3M$ or $COCH_3$ radical, and M is sodium, calcium, magnesium or potassium.

34. A method of treating diseases linked to the survival and growth of motoneurons this method comprising administering to a patient in need thereof an effective amount to prevent or treat such disease of at least one oligosaccharide of formula:

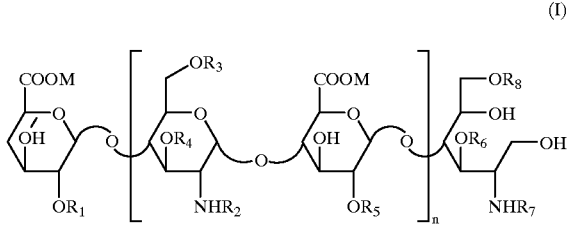

(I)

wherein n is an integer from 0 to 25, each of $R_1$, $R_3$, $R_4$, $R_5$, $R_6$ and $R_8$, which may be identical or different, is hydrogen or an $SO_3M$ radical, each of $R_2$ and $R_7$, which may be identical or different, is hydrogen or an $SO_3M$ or $COCH_3$ radical, and M is sodium, calcium, magnesium or potassium.

* * * * *